(12) United States Patent
Nagasawa et al.

US008808758B2

(10) Patent No.: US 8,808,758 B2
(45) Date of Patent: Aug. 19, 2014

(54) NFAT SIGNAL INHIBITOR AND CALCINEURIN INHIBITOR

(71) Applicant: Kao Corporation, Tokyo (JP)

(72) Inventors: Azumi Nagasawa, Haga-gun (JP);
Shigeru Moriwaki, Haga-gun (JP);
Mitsuyoshi Sakasai, Sumida-ku (JP);
Megumi Matsuoka, Sumida-ku (JP);
Michiyo Sasajima, Haga-gun (JP);
Noriko Ito, Haga-gun (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/922,400

(22) Filed: Jun. 20, 2013

(65) Prior Publication Data

US 2013/0260457 A1  Oct. 3, 2013

Related U.S. Application Data

(62) Division of application No. 13/378,125, filed as application No. PCT/JP2009/002706 on Jun. 15, 2009, now Pat. No. 8,470,376.

(51) Int. Cl.
*A01N 65/00* (2009.01)
*A61K 36/232* (2006.01)
*A61Q 7/00* (2006.01)
*A61K 8/97* (2006.01)
*A61Q 19/00* (2006.01)

(52) U.S. Cl.
CPC .............. *A61K 36/232* (2013.01); *A61Q 7/00* (2013.01); *A61K 8/97* (2013.01); *A61Q 19/00* (2013.01)
USPC ....................................................... 424/725

(58) Field of Classification Search
None
See application file for complete search history.

(56) References Cited

U.S. PATENT DOCUMENTS

| 8,470,376 B2 | 6/2013 | Nagasawa et al. |
| 2003/0186857 A1 | 10/2003 | Kim et al. |
| 2003/0207798 A1 | 11/2003 | Kim et al. |
| 2004/0087496 A1 | 5/2004 | Kim et al. |

FOREIGN PATENT DOCUMENTS

| EP | 2 348 025 A1 | 7/2011 |
| JP | 63-145216 A | 6/1988 |
| JP | 64-038013 | 2/1989 |
| JP | 64-38013 A | 2/1989 |
| JP | 09-194334 A | 7/1997 |
| JP | 3527584 B | 5/2004 |
| JP | 2005-089392 A | 4/2005 |
| WO | WO 01/35914 A1 | 5/2001 |
| WO | WO 2004/041221 A1 | 5/2004 |
| WO | WO 2009/054361 A1 | 4/2009 |

OTHER PUBLICATIONS

International Search Report (ISR) for PCT/JP2009/002706, I.A. fd; Jun. 15, 2009, mailed Aug. 11, 2009, from the Japanese Patent Office, Tokyo, Japan.
International Preliminary Report on Patentability (Chapter I of the Patent Cooperation Treaty) for PCT/JP2009/002706, I.A. fd: Jun. 15, 2009, issued Jan. 17, 2012, from the International Bureau of WIPO, Genera, Switzerland.
Gafter-Gvili, A, et al., "Cyclosporin A-induced hair growth in mice is associated with inhibition of calcineurin-dependent activation of NFAT in follicular keratinocytes," Am J Physiol Cell Physiol 284: C1593-C1603, (Jun. 2003), The American Physiological Society, Bethesda, MD.
Lee, M et al., "Regulation of NFAT activation: a potential therapeutic target for immunosuppresion," Mol Cells 22(1): 1-7 (Aug. 2006), Korean Society for Molecular and Cellular Biology, distributed by Springer, Seoul, Korea.
Feldman, S, "Advances in psoriasis treatment," Dermatol Online J 6(1):4, (Sep. 2000), 19 pages, University of California, Davis, California.
Hultsch, T et al., "Immunomodulation and safety of topical calcineurin inhibitors for the treatment of atopic dermatitis." Dermatology 211(2): 174-187, (Jan. 2005), Karger, Basel, Switzerland.
Molkentin, JD et al., "A calcineurin-dependent transcriptional pathway for cardiac hypertrophy," Cell 93(2): 215-228, (Apr. 1998), Cell Press, Cambridge, MA.
Urushibara, M et al., "The antirheumatic drug leflunomide inhibits osteoclastogenesis by interfering with receptor activator of NF-kappa B ligand-stimulated induction of nuclear factor of activated T cells c1, " Arthritis Rheum, 50(2): 794-804, (Mar. 2004), Wiley-Liss, Inc, NJ.
Takayanagi, H et al., "Induction and activation of the transcription factor NFATc1 (NFAT2) intregrat RANKL signaling in terminal differentiation of osteoclasts," Dev Cell 3(6): 889-901, (Dec. 2002), Cell Press, Cambridge, MA.
Berenbaum, M, "Patterns of furanocoumarin distribution and insect herbivory in the umbelliferae; plant chemistry and community Structure." Ecology 62:1254-1266 (1981), Ecological Society of America, Washington, DC.
Márquez, N et al., "Imperatorin inhibits T-cell proliferation by targeting the transcription factor NFAT,"Planta Med 70(11): 1016-1021, (Nov. 2004), George Thieme, New York.
Gao, Y-P et al., "Potassium Hydroxide Improves Seed Germinatino and Emergence in Five Native Plant Species," HortScience 33: 274-276 (Apr. 1998), American Society for Horticultural Science, Alexandria, VA.
Orpurt, PA, "*Angelica atropurpurea L*, in Indiana,"Proceedings of the Indiana Academy of Science 89: 91-96, (1980), Indiana State Library, Indianapolis, Indiana.
Extended European search report for EP Appl. No. 09846118.9, including the supplementary European search report and the European search opinion dated Oct. 17, 2012, European Patent Office, Munich, Germany.
"Notification of the First Office Action" for Chinese patent application No. 200980159906.5, mailed Jan. 31, 2013, Patent Office of the People's Republic of China, Beijing, China.
Sarker SD et al., "Natural medicine: the genus *Angelica*," Curr Med Chem, Jun. 2004; 11(11)1479-1500, Bentham Science Publishers Ltd., Schipol, The Netherlands.

*Primary Examiner* — Michael Meller
(74) *Attorney, Agent, or Firm* — Sterne, Kessler, Goldstein & Fox P.L.L.C.

(57) ABSTRACT

To provide a drug, an external use composition, and a cosmetic composition, which exhibit an NFAT signal inhibitory action, a calcineurin inhibitory action, and a hair growth-promoting effect.
The NFAT signal inhibitor contains, as an active ingredient, American angelica or an extract thereof.

1 Claim, 1 Drawing Sheet

NFAT SIGNAL INHIBITOR AND CALCINEURIN INHIBITOR

REFERENCE TO SEQUENCE LISTING SUBMITTED ELECTRONICALLY

The content of the electronically submitted substitute sequence listing, file name 2537_0610001_sequencelisting_ascii.txt; size 960 bytes; and date of creation Jun 19, 2013, filed herewith, is incorporated herein by reference in its entirety.

FIELD OF THE INVENTION

The present invention relates to NFAT (nuclear factor of activated T cells) signal inhibitor and to a calcineurin inhibitor.

BACKGROUND OF THE INVENTION

Nuclear factor of activated T cells (hereinafter singly referred to as "NFAT") was discovered as a factor that activates transcription of interleukin-2 (IL-2), which is important for the activation of T cells, and it has been reported that the transcription activity of NFAT is regulated by a serine/threonin phosphatase, calcineurin, which is a target of immunosuppressants such as cyclosporin A (hereinafter simply referred to as "CsA") and tacrolimus (hereinafter simply referred to as "FK506") (see FIG. 2), That is, CsA and FK506 suppress T cell activation by inhibiting the NFAT signal. CsA and FK506 have been approved not only as a transplant immunosuppressant but also as a therapeutic drug for rheumatoid arthritis, psoriasis, and atopic dermatitis, which are known to be involved in the immune system. The system in which when such an NFAT binds to an NFAT binds to an NFAT-binding sequence ("NFAT site" in FIG. 2), transcription of genes downstream of NFAT-binding sequence is promoted, is referred to as "NFAT signal."

On the other hand, it has been reported that a hair-growing (including hair regrowth) effect could be attained through inhibition of NFAT signal (Non-Patent Document 1), It has been also reported that a CsA derivative which inhibits NFAT signal may also serve as a hair growing agent (Patent Documents 1, 2).

Furthermore, NFAT not only has an action on hair growth or an action on the immune system, but is also expressed in many organs and has been recognized as "multifunctional" transcription factor that fulfills critical roles, for example, formation of muscular tissues due to the regulation of heart muscle and skeletal muscle differentiation, formation of a neuro-network in the brain, bone metabolism due to the regulation of osteoblastic differentiation, and the like.

The role of NFAT signal that affects the living body is as discussed above, but it has been reported that when the NFAT signal is inhibited, an immunosuppressive action (Non-Patent Document 2), treatment of psoriasis (Non-Patent Document 3), treatment of atopic dermatitis (Non-Patent Document 4), suppression of (cardiac) muscle hypertrophy (Non-Patent Document 5), a potential of an anti-rheumatic drug (Non-Patent Document 6), a suppressive action on osteoclast differentiation (Non-Patent Document 7), and the like can be expected. Furthermore, since NFAT is mediated by a pathway to produce immune cytokine IL-2, as described above, an NFAT signal inhibitor is useful for the treatment or prevention of diseases that are considered to involve immune cytokine, including autoimmune disease.

Examples of such target diseases include various cancers, various leukemia, various hepatitis, various infections, systemic lupus erythematosus, inflammatory bowel diseases (ulcerative colitis, Crohn's disease), multiple sclerosis, insulin-dependent diabetes, peptic ulcer, septic shock, tuberculosis, infertility, arteriosclerosis, Behcet's disease, asthma, nephritis, acute bacterial meningitis, acute myocardial infarction, acute pancreatitis, acute viral encephalitis, adult acute respiratory distress syndrome, bacterial pneumonia, chronic pancreatitis, peripheral vascular diseases, sepsis, interstitial liver diseases, situational ileitis, and multiple sclerosis, Therefore, when a novel NFAT signal inhibitor is identified, uses thereof as an immunosuppressant, a therapeutic agent for psoriasis, a therapeutic agent for atopic dermatitis, a suppressant for (cardiac) muscle hypertrophy, an anti-rheumatic drug, a therapeutic agent for bone metabolic diseases, and novel medicinal uses such as listed above are expected. Furthermore, when a novel NFAT signal inhibitor is identified, uses thereof as a quasi-drug such as a hair-growing agent or a hair regrowth promoting agent, and cosmetic uses are expected.

Meanwhile, there has been reported that extracts of plants belonging to the genus *Angelica* are recognized to have a hair-growing, hair regrowth, or hair-nourishing effect (Patent Documents 3 to 6), Specifically, Patent Document 3 discloses a hair-nourishing/hair-growing agent containing a Dong Quai (*Angelica sinensis*) extract. Patent Document 4 discloses a hair-nourishing agent containing an essential oil of *Angelica glauca*. Patent Document 5 discloses a hair regrowth and hair growth promoting material containing an extract of Bai Zhi (*Angelica dahurica* Benth. Et Hook). Patent Document 6 discloses a hair beautifying material such as a hair-growing and hair-nourishing agent containing an extract of Ashitaba (*Angelica* Keiskei Koidz).

However, there has been no report that suggests the relationship between NFAT signal and the aforementioned plants belonging to the genus *Angelica*. Among plants belonging to the genus *Angelica*, American angelica (*Angelica atropurpurea*) has never been known to have a hair growth, a hair regrowth action, or the like, and use of American angelica (i.e., application to the skin) has never been reported.

PRIOR ART DOCUMENT

Patent Document

Patent Document 1: WO 01/035914 (JP-A-2003-514000)
Patent Document 2: WO 2004/041221 (JP-A-2006-508103)
Patent Document 3: JP-B-3527584
Patent Document 4: JP-A-2005-89392
Patent Document 5: JP-A-01-38013
Patent Document 6: JP-A-63-145216

Non-Patent Document

Non-Patent Document 1: Gafter-Gvili A., Sredni B., Gal R., Gafter U., and Kalechman Y., "Cyclosporin A-induced hair growth in mice is associated with inhibition of calcineurin-dependent activation of NFAT in follicular keratinocytes," Am. J. Physiol, Cell Physiol., 284: C1593-C603, 2003
Non-Patent Document 2: Lee M. and Park J., "Regulation of NFAT activation: a potential therapeutic target for immunosuppression," Mol. Cells, 22: 1-7, 2006
Non-Patent Document 3: Feldman S., "Advances in psoriasis treatment," Dermatol Online J., 6: 4, 2000
Non-Patent Document 4: Hultsch T., "Immunomodulation and safety of topical calcineurin inhibitors for the treatment of atopic dermatitis," Dermatology, 211: 2, 2005

Non-Patent Document 5: Molkentin J. D., Lu J. R., Antos C. L., Markham B., Richardson J., Robbins J., Grant S. R., and Olson E. N., "A calcineurin-dependent transcriptional pathway for cardiac hypertrophy," Cell, 93: 215-228, 1998

Non-Patent Document 6: Urushibara M., Takayanagi H., Koga T., Kim S., Isobe M., Morishita Y., Nakagawa T., Loeffler M., Kodama T., Kurosawa H., and Taniguchi T., "Antirheumatic drug, leflunomide, inhibits osteoclastgenesis by interfering with RANKL-stimulated induction of NFATcl," Arthritis and Rheumatism, 50: 794-804, 2004

Non-Patent Document 7: Takayanagi H., Kim S., Koga T., Nishina H., Isshiki M., Yoshida H., Saiura A., Isobe M., Yokochi T., Inoue J., Wagner E. F., Mak T. W., Kodama. T., and Taniguchi T., "Induction and activation of the transcription factor NFATcl (NFAT2) integrate RANKL signal in terminal differentiation of osteoclasts," Developmental Cell, 3: 889-901, 2002

SUMMARY OF THE INVENTION

The present invention relates to the following (1) to (9):

(1) an NFAT signal inhibitor containing, as an active ingredient, American angelica or an extract thereof;

(2) a calcineurin inhibitor containing, as an active ingredient, American angelica or an extract thereof;

(3) a composition for external use (hereinafter may be referred to as an "external use composition") containing, as an active ingredient, American angelica or an extract thereof;

(4) a hair growth promoter containing, as an active ingredient, American angelica or an extract thereof;

(5) a method for inhibiting NFAT signal, characterized in that the method includes bringing American angelica or an extract thereof into contact with a target human cell or tissue;

(6) a method for inhibiting calcineurin, characterized in that the method includes bringing American angelica or an extract thereof into contact with a target human cell or tissue;

(7) a method for promoting hair growth, characterized in that the method includes applying American angelica or an extract thereof to the scalp of a target human subject;

(8) Use of American angelica or an extract thereof for producing NFAT signal inhibitor; and (9) Use of American angelica or an extract thereof for producing a calcineurin inhibitor.

DETAILED DESCRIPTION OF THE INVENTION

Figure 1:
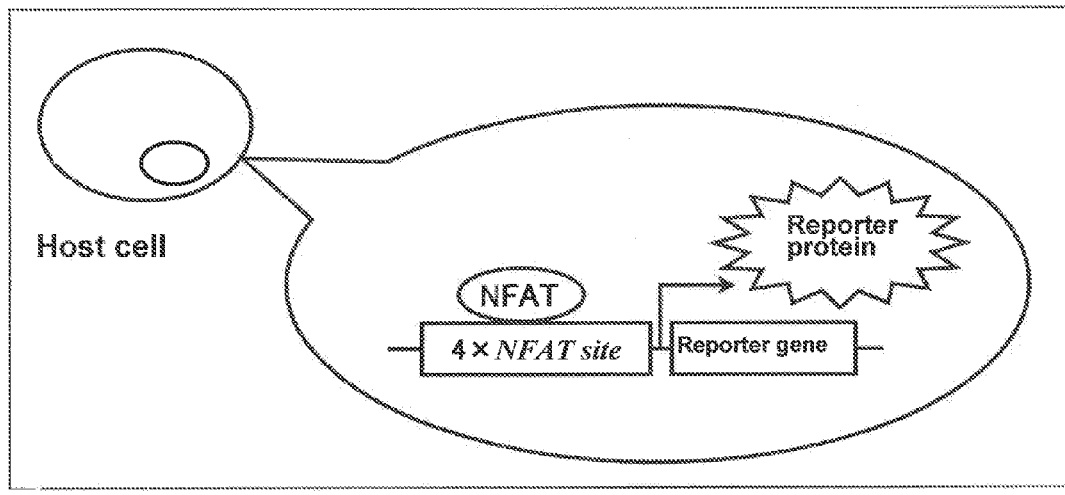
[FIG. 1] A sketch of a feature of a reporter assay, which is an exemplary method for assaying NFAT signal inhibitory action.

The present invention relates to provision of a pharmaceutical product, an external use composition, and a cosmetic product and the like, each of which has an NFAT signal inhibitory action, a calcineurin inhibitory action, and a hair-growing action.

The inventors of the present invention have created a system for evaluating the NFAT signal transduction action, and comprehensively analyzed a variety of plants in terms of NFAT signal inhibitory action. As a result, the inventors have found that American angelica or an extract thereof has an excellent NFAT signal inhibitory action and calcineurin inhibitory action, and thus is useful for a pharmaceutical product, a cosmetic product, and the like which are effective for prevention and treatment of a disease caused by an enhancement of the NFAT-induced transcription promoting activity or a disease caused by an enhancement of calcineurin-related signal transduction, or which exhibits hair growing, hair nourishing effect, or the like.

Because the active ingredient of the NFAT signal inhibitor, calcineurin inhibitor, external use composition, and hair growth promoter of the present invention originates from American angelica—a natural substance—or an ingredient derived therefrom, no health safety concerns arise. According to the NFAT signal inhibitor or the like, a disease caused by an enhancement of NFAT-induced transcription promoting activity, or a disease caused by an enhancement of calcineurin-related signal transduction can be prevented or treated, and hair growing or hair nourishing can be attained.

In the present invention, American angelica refers to a plant having a botanical name of *Angelica atropurpurea* and belonging to the family Apiaceae.

In the present invention, the whole plant, leaves, stems, flowers, fruit, seeds, rhizomes, or roots, etc. American angelica, or a dried/pulverized product thereof may be employed.

The extract of American angelica may be produced through extraction of the aforementioned available parts, preferably rhizomes or roots without any further processing or with drying to pieces of appropriate dimensions or pulverization. The extract also includes a diluted liquid thereof, a concentrated liquid thereof, a dried powder thereof, or a high-activity fraction (ingredient) thereof obtained through further separation/purification.

The extraction may be performed through solvent extraction where the plant is immersed in a solvent at room temperature or an elevated temperature or solvent extraction by means of an extracting apparatus such as a Soxhlet's extractor. Alternatively, extraction with distillation such as steam distillation, supercritical extraction employing supercritical $CO_2$ gas, expression, etc. may also be employed.

The extraction solvent used for recovering the plant extract may be a polar solvent or a non-polar solvent. Examples of the extraction solvent include water; alcohols such as methanol, ethanol, propanol, and butanol; polyols such as propylene glycol and butylene glycol; ketones such as acetone and methyl ethyl ketone; esters such as methyl acetate and ethyl acetate; linear or cyclic ethers such as tetrahydrofuran and diethyl ether; polyethers such as polyethylene glycol; hydrocarbons such as squalane, hexane, cyclohexane, and petroleum ether; aromatic hydrocarbons such as toluene; halohydrocarbons such as dichloromethane, chloroform, and dichloroethane; and carbon dioxide. Alternatively, two or more members of the aforementioned solvents may be used in combination. For example, 20 to 80%, aqueous ethanol, benzene: ethyl acetate (4:1) mixture, or aqueous 1,3-butylene glycol may be used.

Among them, anhydrous alcohol is preferred, with anhydrous ethanol being more preferred.

American angelica is known to contain photosensitizing substances such as 8-methoxypsoralen (8-MOP) and 5-methoxypsoralen (5-MOP). In order to remove such photosensitizing substances, American angelica is preferably subjected to preliminary washing with aqueous ethanol before carrying out the aforementioned solvent extraction. No particular limitation is imposed on the aqueous ethanol employed in preliminary washing, and, for example, 10 to 60 vol. % aqueous ethanol may be used. Ethanol employed in extraction preferably has an ethanol content higher than that of the ethanol solvent employed in preliminary washing. More preferably anhydrous ethanol is used.

In order to reduce the photosensitizing substance level to the detection limit or lower, preliminary washing with 25 to 45 vol. % aqueous ethanol is preferably performed at a plurality of times for example 3 or more times. No particular limitation is imposed on the number of times of preliminary washing. However, the number of times is preferably 9 or less, for maintaining, at high levels, hair growth activity, NFAT signal inhibitory activity, and calcineurin inhibitory activity attained by the active ingredient(s). In other words, by performing 2 to 9 times preliminary washing with 25 to 45 vol. % aqueous ethanol, the photosensitizing substance level can be considerably reduced, and hair growth activity, NFAT signal inhibitory activity, and calcineurin inhibitory activity can be maintained at high levels.

Examples of the means for separation/purification of the extract include activated carbon treatment, liquid-liquid separation, column chromatography, liquid chromatography, gel filtration, and precision distillation.

The American angelica extract of the present invention may be used in various forms. Examples include as-recovered extracts or fraction, diluted liquids with an appropriate solvent, concentrated extracts, dried powder, and paste. Alternatively, a lyophilized product of the extract may be reconstituted upon use with a solvent which is generally employed in solvent extraction such as water, ethanol, propylene glycol, butylene glycol, water-ethanol mixture, water-propylene glycol mixture, or water-butylene glycol mixture. Yet alternatively, the extract may be encapsulated by a vesicle structure such as a liposome or by a microcapsule.

As described in the Examples hereinbelow, American angelica or an extract thereof has an NFAT signal inhibitory action, a calcineurin inhibitory action, and a hair-growing action.

The NFAT signal inhibitory action can be evaluated by using the NFAT signal inhibitory rate as an index. An extract of American angelica exhibits a percent NFAT signal inhibition of 101.3%. The NFAT signal inhibitory rate briefly means a percentage ratio of drop in transcription activity attributed to NFAT when an Angelica extract is added, with respect to transcription activity attributed to NFAT when no Angelica extract is added.

Figure 2:
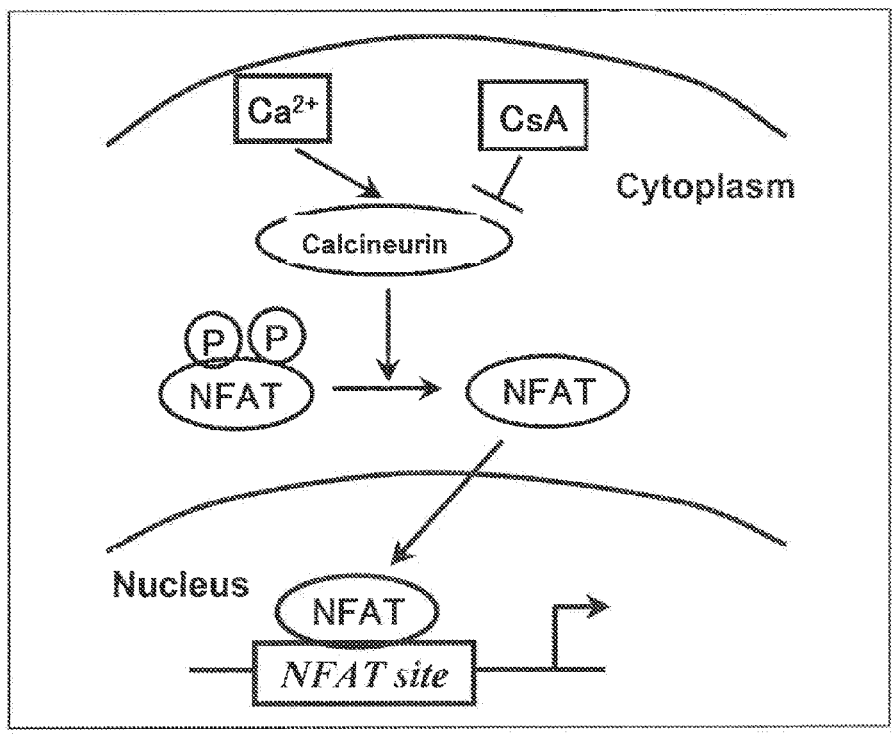
[FIG. 2] A sketch of a feature of NFAT signal, showing bonding between NFAT and an NFAT-binding site as well as promotion of transcription of a gene portion located on the downstream thereof.

No particular limitation is imposed on the method of determining the NFAT signal inhibitory action. For example, there may be employed a reporter assay employing a host containing a plasmid having a known NFAT-binding sequence and a reporter gene ligated to the downstream of the NFAT-binding sequence (see FIG. 2). Notably, since the NFAT activity depends on calcium ions, reporter assay is performed while calcium ions are caused to be incorporated into the host. No particular limitation is imposed on the reporter gene, and any reporter gene may be used, so long as the gene has been used in conventional biological experiments. Examples of the reporter gene include a luciferase gene, a β-glucuronidase gene (GUS gene), and a green fluorescent protein gene (GFP gene).

The NFAT-binding sequence means an oligonucleotide formed of a sequence to which NFAT has been bound. Examples of the sequence include a nucleotide sequence GGAGGAAAAACTGTTTCATACAGAAGGCGT (pN-FAT-Luc, Stratagene, SEQ ID NO: 1). Into the aforementioned plasmid, a plurality of sets of an NFAT-binding sequence (one set) linked to one another may be incorporated. When a plurality of NFAT-binding sequences is used, transcription-promoting activity attributed to NFAT can be determined at higher sensitivity. The aforementioned NFAT signal inhibitory rate is calculated from data obtained through the reporter assay.

The calcineurin inhibitory action can be evaluated as a percent inhibition of dephosphorylation activity attributed to calcineurin. An extract of American angelica exhibits a percent calcineurin activity inhibition of 43.5%. The calcineurin inhibitory rate briefly means a percentage ratio of drop in activity of dephosphorylation of phosphorylated peptide (substrate) attributed to calcineurin when an Angelica extract is added, with respect to the dephosphorylation activity when no Angelica extract is added.

Calcineurin ($Ca^{2+}$/calmodulin-regulated Ser/Thr phosphatase) is involved in $Ca^{2+}$-mediated signal transduction, and causes release of a specific phosphate group of a specific phosphorylated protein including NFAT. No particular limitation is imposed on the method of determining the calcineurin inhibitory action. For example, there may be employed a detection method in which release of a phosphate group from a substrate is detected, wherein the substrate is, for example, a known phosphorylated peptide serving as a substrate for calcineurin. Examples of phosphorylated peptide serving as a substrate for calcineurin include RII phosphorylated peptide (DLDVPIPGRFDRV[pS]VAAE). Thus, calcineurin inhibitory activity can be determined by causing an Angelica extract to act on a substrate in the presence of calcineurin and assaying the released phosphate. No particular limitation is imposed on the method of quantitating the release phosphate. In one quantitating method, a malachite green reagent is used.

The hair-growing action means an action on hair follicles and achieves acceleration of hair shaft elongation, an increase of hair thickness, acceleration of transition from the telogen phase to the anagen phase in the hair growth cycle, inhibition of transition from the anagen phase to the catagen phase, and the like, to thereby increase the amount of hair. Accordingly, hair growth is meant to include the concepts of hair regrowth, hair nourishing and prevention of alopecia. There are no particular limitations on the method for measuring hair-growing action, but an example may be a method that subjecting isolated hair follicles to organ culture and measuring the amount of elongation of hair shaft during the culture period.

In the present invention, the NFAT signal inhibitory action means an action which targets NFAT directly or indirectly to thereby reduce transcription positively controlled by NFAT (transcription promoting activity), whereby NFAT signal is inhibited in cells and tissues. Thus, through bringing American angelica or an extract thereof into contact with the target cells or tissues; e.g., human cells or tissues, the NFAT signal in the cells or tissues can be inhibited. As a result, in the cells or tissues, various gene expressions triggered by NFAT signal can be suppressed at a transcription level.

Therefore, the NFAT signal inhibitor of the present invention may be used as an agent for treating or preventing a condition or disease which is caused by an enhancement of the NFAT-induced transcription promoting activity. Examples of the condition or disease which is caused by an enhancement of the NFAT-induced transcription promoting activity include immune system-related diseases, psoriasis, atopic dermatitis, muscular hypertrophy including cardiomuscular hypertrophy, rheumatoid arthritis, bone metabolic diseases, various cancers, various leukemia, various hepatitis, various infections, systemic lupus erythematosus, inflammatory bowel diseases (ulcerative colitis and Crohn's disease), multiple sclerosis, insulin-dependent diabetes, peptic ulcer, septic shock, tuberculosis, sterility, arteriosclerosis, Behcet's disease, asthma, nephritis, acute bacterial meningitis, acute heart infarction, acute pancreatitis, acute viral encephalitis, adult acute respiratory distress syndrome, bacterial pneumonia, chronic pancreatitis, peripheral vascular diseases, sepsis, interstitial liver diseases, situational ileitis, and multiple sclerosis.

As described above, through inhibition of NFAT signal, a hair growing (including hair regrowth) effect is prospected. As shown in Example 4, an extract of American angelica was found to have a hair growth promotion action. Thus, the NFAT signal inhibitor of the present invention may be used as a hair-growing agent or a hair-regrowth promoting agent.

The calcineurin inhibitory action means an action which reduces calcineurin activity. Through this action, signal transduction attributed to calcineurin in cells or tissues can be inhibited. In other words, through bringing American angelica or an extract thereof into contact with the target cells or tissues for example, human cells or tissues, signal transduction attributed to calcineurin in the cells or tissues can be inhibited, whereby various events triggered by signal transduction attributed to calcineurin in the cells or tissues can be suppressed.

Therefore, the calcineurin inhibitor of the present invention may be used as an agent for treating or preventing a condition or disease which is caused by excessively promoted signal transduction attributed to calcineurin. In addition to conditions or diseases caused by enhanced transcription-promoting activity attributed to NFAT exemplified above, examples of the condition or disease which is caused by excessively promoted signal transduction attributed to calcineurin include various allergic diseases, and mental disorders such as schizophrenia.

As described above, American angelica or an extract thereof may be employed as a drug, an external use composition, a cosmetic product, and the like which exhibit an NFAT signal inhibitory action, a calcineurin inhibitory action, or a hair growing action.

When American angelica or an extract thereof is used as a drug, no particular limitation is imposed on the dosage form. Examples of the dosage form include solid preparations such as powder, granules, capsule, pill, and tablet; liquid preparations such as solution, suspension, and emulsion; and ointment.

When American angelica or an extract thereof is used as a peroral drug, the drug may be produced through a routine method, by adding, to American angelica or an extract thereof, additives generally employed in accordance with the form of the peroral drug, such as a diluent, a disintegrant, a binder, a lubricant, a surfactant, alcohol, water, water-soluble polymer, a sweetener, a corrigent, and a sour agent. Examples of the peroral drug include an immunosuppressant, a psoriasis therapeutic agent, a (cardiac) muscular hypertrophy suppressor, and an anti-rheumatic drug.

When American angelica or an extract thereof is used as a percutaneous drug, the drug may be produced through a routine method, by adding, to American angelica or an extract thereof, additives generally employed in accordance with the form of the percutaneous drug, such as oily substrates (e.g., vegetable oil, animal oil, synthetic oil, fatty acid, and natural or synthetic glyceride), a lubricant, a surfactant, alcohol, and a thickener. Examples of the percutaneous drug include an immunosuppressant, a psoriasis therapeutic agent, an atopic dermatitis therapeutic agent, and a hair growth promoting agent.

The external use composition and the hair growing agent are used as, for example, a quasi-drug for skin, and are provided as a preparation suitable for the purpose of use. No particular limitation is imposed on the form of the preparation, and specific examples include ointment, solution, extract, lotion, tonic, spray, and emulsion.

Into the quasi-drug, in addition to American angelica or an extract thereof, there may be incorporated pharmaceutically acceptable carriers such as an aid, a stabilizer, a humectant, an emulsifier, an absorption-enhancer, and a surfactant, in desired any combination. Also, the hair growing agent may further contain, in addition to the aforementioned active ingredients and in accordance with need, an appropriate amount of a pharmaceutically active hair-nourishing agent which is generally employed in such products, in order to enhance hair-growing effect. Examples of the hair-nourishing agent include a hair follicle-activating agent, a blood flow-promoting agent, an antiseptic agent, an anti-inflammatory agent, a humectant, an anti-seborrheic agent, a local stimulant, an anti-androgenic agent, a potassium-channel-opener, and an anti-oxidant. Thus, the target effect can be enhanced. Examples of the hair follicle-activating agent include flavanols, N-acetyl-L-methionine, pantothenic acid or a derivative thereof, adenosine or a derivative thereof, potassium aspartate, glycerin pentadecanoate, 6-benzylaminopurin, and mononitroguaiacol sodium. Examples of the blood flow-promoting agent include carbon dioxide, nicotinamide, benzyl nicotinate, *Swertia Japonica* extract, ginseng extract, carpronium chloride, vitamin E or a derivative thereof. Examples of the antiseptic agent include isopropylmethyl phenol, benzalkonium chloride, Octopyrox, zinc pyrithione, and hinokitiol. Examples of the anti-inflammatory agent include licorice extract, glycyrrhizinic acid or a derivative thereof, glycyrrhetinic acid or a derivative thereof, azulene, guaiazulene, *Scutellaria Baicalensis* extract, matricaria extract, *Sasa Veitchii* extract, birch extract, marrow extract, peach leaf extract, and Yarrow extract. Examples of the humectant include hypericum extract, oats extract, glycerin, polyanthes tuberosa polysaccharide, Cordyceps extract, isodonis herba extract, barley extract, grape extract, propylene glycol, platycodon extract, and coix extract. Examples of the anti-seborrheic agent include sulfur, lecithin, polygonum root extract, and thioxolone. Examples of the local stimulant include camphor and capscium tincture. Examples of the anti-androgenic agent include cyproterone acetate, 11α-hydroxyprogesterone, flutamide, 3-deoxyadenosine, chlormadinone acetate, ethynylestradiol, spironolactone, episterone, finasteride, aloe, Japanese pepper, clove extract, cuachalalate extract, and Asian ginseng. Examples of the potassium-channel-opener include minoxidil, cromakalim, diazoxide and a derivative thereof, and pinacidil. Examples of the anti-oxidant include *Camellia Sinensis* extract, tea extract, rose extract, *Engelhardia* extract, vitamin C or a derivative thereof, erythorbic acid, propyl gallate, and dibutylhydroxytoluene.

When American angelica or an extract thereof is used in a cosmetic composition, no particular limitation is imposed on the product fort, Examples of the product form include O/W or W/O emulsion cosmetic compositions, cream, lotion, gel, foam, essence, foundation, pack, stick, and powder. In addition to the plant extract, the cosmetic composition may further contain a combination of additives generally employed as cosmetic composition ingredients. Examples of such additives include oil, a surfactant, a UV-absorber, alcohol, a chelating agent, a pH-regulator, an antiseptic agent, a thickener, a dye, a perfume, and a various skin nutrients. Specific examples include the following efficient drug ingredients employed in skin cosmetic compositions: UV-absorbing agents such as microparticulated zinc oxide, titanium oxide, Parsol MCX, and Parsol 1789; vitamins such as ascorbic acid; humectants such as sodium hyaluronate, petrolatum, glycerin, and urea; hormone agents; skin-whitening ingredients such as kojic acid, arbutin, placenta extract, and rucinol; substances which inhibit production/release of chemical messengers such as steroid drugs, arachidonic acid metabolits, and histamine(indomethacin, ibuprofen); anti-inflammatory agents such as a receptor antagonist; anti-androgenic agents; sebum secretion inhibitors such as vitamin. A acid, royal jelly extract, and royal jelly acid; peripheral vasodilators such as tocopherol nicotinate, alprostadil, isoxsuprine hydrochloride, and tolazoline hydrochloride, and substances which have peripheral vasodilator-like action such as carbon dioxide; blood flow-promoting agents such as minoxidil, carpronium chloride, capscium tincture, a vitamin E derivative, ginko biloba extract, and *Swertia Japonica* extract; cellular-function-activating agents such as glycerin pentadecanoate and nicotinamide; antiseptic agents such as hinokitiol, L-menthol, and isopropylmethyl phenol; drugs such as glycyrrhizinic acid or a derivative thereof, or a salt of any of these; and ceramide or ceramide-like compounds.

If needed, the aforementioned drug, quasi-drug, and cosmetic product may appropriately contain, additives in combination. Examples of such additives include powders such as chalk, talc, fuller's earth, kaolin, starch, rubber, and colloidal silica sodium polyacrylate; oil or oily substances such as mineral oil, vegetable oil, and silicone oil; emulsifying agents such as sorbitan trioleate, sorbitan tristearate, glycerol monooleate, a polymeric silicone surfactant; antiseptic agents such as a p-hydroxybenzoate ester; anti-oxidants such as butylhydroxytoluene; humectants such as glycerol, sorbitol, 2-pyrrolidone-5-carboxylate, dibutyl phthalate, gelatin, and polyethylene glycol; buffers such as lactic acid-base (e.g., triethanolamine or sodium hydroxide); surfactants such as glycerin fatty acid ester, sorbitan fatty acid ester, sucrose fatty acid ester, and alkyl glucoside; waxes such as beeswax, ozokerite wax, and paraffin wax; thickeners; activity-enhancers; colorants; and perfumes.

The aforementioned drug, quasi-drug, or cosmetic composition generally contains American angelica or an extract thereof in an amount (calculated as dried product) of 0.00001 to 5 wt.-%, with respect to the total amount of the drug, quasi-drug, or cosmetic composition, particularly preferably 0.0001 to 0.1 wt. %. When American angelica or an extract thereof is used in a drug, the daily dose thereof (solid content) is generally 1 mg to 1 g/day for an adult. In the case of an external use composition, the dose is preferably 0.01 mg to 1 g/day. In application, the amount of the external use composition of the present invention, which varies depending on the active ingredient content, is preferably 1 to 20 mg per 1 cm$^2$ of skin area in the case of cream or ointment, and 1 to 20 mg in the case of solution.

EXAMPLES

Hereinafter, the present invention will next be more specifically explained by way of examples However, the present invention is not intended to have the technical scope limited to these Examples.

Example 1

Production of Plant Extract

In the present Example, an extract of American angelica was produced. Firstly, 95% ethanol (100 mL) was added to 10 g of American angelica root (produced in the U.S.A.), and the mixture was allowed to stand at room temperature for 7 days. Thereafter, the mixture was subjected to extraction, and the recovered liquid was filtered, to thereby yield 80 mL of an extract, The amount of evaporation reside was 0.7 w/v %.

Example 2

NFAT Signal Inhibitory Effect

In the present Example, an evaluation system was established for detecting an NFAT signal inhibitory effect. The NFAT signal inhibitory effect of the plant extract produced in Example 1 was detected by means of the evaluation system.
(1) Material and Method for Establishing the Evaluation System
Cell Culture In this evaluation system, human kidney cells (HEK293) were purchased from ATCC (American Type Culture Collection) and used. The HEK293 cells were cultured in DMEM (high glucose, 10% heat-inactivated FBS) at 37° C. under 5% $CO_2$ condition.
Plasmid and Transfection In this evaluation system, HEK293 cells transfected with a plasmid having Photinus pyralis luciferase introduced into the downstream of the NFAT-binding sequence, pNFAT-Luc (Stratagene), were used. More specifically, the pNFAT-Luc (Stratagene), in which Photinus pyralis luciferase gene was introduced in the downstream of 4 copies of the NFAT-binding sequence, was transfected into HEK293 cells for an evaluation of the NFAT transcription activity. Furthermore, for the purpose of eliminating fluctuation due to the transfection efficiency, pRL-CMV (Promega) having renila luciferase introduced in the downstream of CMV promoter, was simultaneously transected so as to correct for the signal derived from Photinus pyralis luciferase.

Transfection was carried out by using Lipofect AMINE 2000 reagent (Invitrogen) according to the instruction manual. The medium was exchanged eight hours after the transfection, and the system was incubated overnight. Thereafter, the plant extract produced in Example 1 (0.5 vol. %) was added to the culture, and after elapse of one hour, 1-µM ionomycin was added. Eight hours after addition of ionomycin, luciferase reporter assay was carried out. Ionomycin is an ionophore having specificity to calcium ions and is known to be a drug which injects calcium ions into cells. Through addition of ionomycin, calcineurin—calcium ion-dependent phosphatase—was activated, and the transcription, activity of NFAT was also elevated. Therefore, this system was thought to be suited for retrieving an NFAT signal activation inhibitor.
Luciferase Reporter Assay The luciferase reporter assay was carried out using Dual-Glo Luciferase Assay System (Promega) according to the instruction manual. That is, the medium was removed, and then Dual-Glo Luciferase reagent which had been diluted two times with PBS, was added thereto. The system was stirred, and after 20 minutes, the Photinus pyralis luciferase activity was measured. Thereafter, an equal amount of Dual-Glo Stop & Glo reagent was added to the system, the mixture was stirred, and then the Renilla luciferase activity was measured. The luciferase activity measurement was carried out using Mini Lumat LB 9506 (EG&G BERTHOLD), and the amount of luminescence by luciferase was quantitatively detected. For both luciferases, the duration for luciferase activity measurement was set to 2 seconds.
Calculation of Percent NFAT Signal Inhibition All of the NFAT transcription activity values (Photinus pyralis luciferase activity) were corrected by dividing the values of Renilla reniformis luciferase activity introduced for the transfection efficiency correction. Thereafter, the NFAT signal inhibitory rate was calculated by the following equation.

Percent NFAT signal inhibitory rate (%)=100−(test sample and ionomycin addition group−non-stimulated group)/(ionomycin addition group−non-stimulated group)×100.

Based on the calculation described above, calculation can be made on by what percent (%) the test sample inhibited the NFAT signal activation induced by ionomycin stimulation.

Results

The American angelica extract produced in Example 1 was found to exhibit a percent NFAT signal inhibition of 101.3%. Thus, the American angelica extract was found to inhibit NFAT signal. That is, the American angelica extract can suppress transcription positively controlled by NFAT. Thus, the American angelica extract produced in Example 1 was found to serve as an excellent NFAT signal inhibitor and was identified as a candidate substance for, for example, an immunosuppressant, a psoriasis therapeutic agent, an atopic dermatitis therapeutic agent, a hair growth promoter, a hair growth promoting agent, a (cardiac) muscular hypertrophy suppressor, or an anti-rheumatic drug.

Example 3

Comparison of Percent NFAT Signal Inhibition Among Plants Belonging to the Genus *Angelica*

In the present Example, extracts were prepared from a variety of plants belonging to the genus *Angelica*, and NFAT signal inhibitory action was compared among them. The extracts were prepared as follows.

<American angelica>

To 8 g of dry roots of American angelica (*Angelica atropurpurea*) (produced in the U.S.A.), 80 mL of 95 vol. % ethanol was added. The mixture was allowed to stand at room temperature for 7 days for extraction. The product was filtered, thereby yield an extract (evaporation residue: 1.0 wt./vol. %)

<Touki>

To 8 g of dry roots of Touki (*Angelica acutiloba*) (produced in Japan), 80 mL of 95 vol. % ethanol was added. The mixture was allowed to stand at room temperature for 7 days for extraction. The product was filtered, thereby yield an extract (evaporation residue: 0.6 wt./vol. %).

<Ashitaba>

To 8 g of dry leaves of Ashitaba (*Angelica keiskei*) (produced in Japan), 80 mL of 95 vol. % ethanol was added. The mixture was allowed to stand at room temperature for 7 days for extraction. The product was filtered, thereby yield an extract (evaporation residue: 1.9 wt./vol. %).

<Byakushi>

To 8 g of dry roots of Byakushi (*Angelica dahurica*) (produced in China), 80 mL of 95 vol. % ethanol was added. The mixture was allowed to stand at room temperature for 7 days for extraction. The product was filtered, thereby yield an extract (evaporation residue: 0.5 wt./vol. %).

<Karatouki>

To 8 g of dry roots of Karatouki (*Angelica sinensis*) (produced in China), 80 mL of 95 vol. % ethanol was added. The mixture was allowed to stand at room temperature for 7 days for extraction. The product was filtered, thereby yield an extract (evaporation residue: 0.7 wt./vol. %), <Europe touki>

To 8 g of dry roots of Europa touki (*Angelica archangelica*) (produced in France), 80 mL of 95 vol. % ethanol was added. The mixture was allowed to stand at room temperature for 7 days for extraction. The product was filtered, thereby yield an extract (evaporation residue: 1.0 wt./vol. %).

The thus-prepared six extracts of the plants belonging to the genus *Angelica* were subjected to the same test as performed in Example 2, to thereby calculate percent NFAT signal inhibition. Table 1 shows the results.

TABLE 1

| Japanese name | Scientific name | NFAT signal inhibition at solid concentration of 0.005 wt. % (% of inhibition) |
|---|---|---|
| American angelica | *Angelica atropurpurea* | 95.5 |
| Touki | *Angelica acutiloba* | 22.6 |
| Ashitaba | *Angelica keiskei* | 3.2 |
| Byakushi | *Angelica dahurica* | 9.7 |
| Karatouki | *Angelica sinensis* | 52.6 |
| Europe touki | *Angelica archangelica* | 23.7 |

As is clear from Table 1, among the extracts of the plants belonging to the genus *Angelica*, the extract of American angelica exhibited remarkably high percent NFAT signal inhibition, as compared with other extracts. Thus, the American angelica extract was found to serve as an excellent NFAT signal inhibitor as compared with other extracts, and was identified as a candidate substance for, for example, an immunosuppressant, a psoriasis therapeutic agent, an atopic dermatitis therapeutic agent, a hair-growing agent, a hair regrowing agent, a (cardiac) muscular hypertrophy suppressor, or an anti-rheumatic drug.

Example 4

In the present Example, the hair-growing effect of the plant extract produced in Example 1 was assessed by means of an in vitro experiment system which can detect the hair-growing effect of the sample.

Evaluation of Hair Shaft Elongation by Swine Hair Follicle Organ-culture

The skin of buttocks of a pig for meat was cut into pieces of appropriate sizes, and excessive adipose tissue was removed. The pigskin was disinfected by immersing in a Hibitane solution (5% Hibitane solution (Sumitomo Pharm.) diluted to 5 to 20 times with water) for 5 minutes to 10 minutes, under sterile conditions, and then was washed several times with D-PBS. Subsequently, hair follicles were isolated from the washed pig skin under a stereoscopic microscope, and the hair follicles were collected in William's Medium E medium (Invitrogen).

The isolated hair follicles were dispensed on a 24-well culture plate with 400 μL of William's Medium E medium (containing 1% Penicillin-Streptomycin solution, (Invitrogen)) such that one follicle was placed in one well. The hair follicles were cultured for 8 days at 37° C. under 5% $CO_2$ condition. During the culturing, the medium exchange was carried out at an interval of one day or two days.

To the aforementioned medium, the American angelica extract produced in Example 1 was added (solid content: 0.0001 wt. %) and cultured for 8 days. A control group, containing ethanol instead of the extract, was simultaneously cultured. On culture day 0 (start) and day 8, the stereoscopic microscopic image of the culture was taken by means of a CCD camera (pixera model. No. PVC 100C), and from those images, the length from the base of the hair bulb to the hair shaft was measured. Then, taking the difference between the hair length of the solvent control group before culturing and that after culturing as 100%, the hair shaft elongation ratios of American angelica extract (Example 1)-added group was calculated.

As a result, the American angelica extract-added group exhibited a percent hair elongation of 113.1%, with respect to the solvent control group. Thus, the American angelica extract was found to exhibit hair-growing effect. That is, the American angelica extract can be used as an excellent hair-growing agent and as an external use composition which exhibits excellent hair-growing effect.

Example 5

In the present Example, the calcineurin inhibitory effect of the plant extract produced in Example 1 was assessed by means of a commercially available kit which can detect the calcineurin inhibitory effect of the sample.

Measurement of Calcineurin Activity

Calcineurin enzymatic activity was determined by means of Calcineurin assay kit (BIOMOL) according to the instruction manual. In the assay, recombinant human calcineurin was employed as an enzyme, and RII phosphorylated peptide (DLDVPIPGRFDRV[pS]VAAE)—calcineurin substrate peptide—was employed as a substrate. In the assay, the American angelica extract produced in Example 1 was used at a concentration of 1 vol. %. The calcineurin activity inhibitory effect of the American angelica extract produced in Example 1 was calculated by inhibitory effect, taking the calcineurin activity of the solvent control as 100%.

As a result, the American angelica extract-added group exhibited a calcineurin activity inhibitory rate of 43.50, with respect to the solvent control group. Thus, the American angelica extract was found to inhibit calcineurin activity. That is, the American angelica extract can suppress a signal transduction system involving calcineurin. Therefore, the American angelica extract produced in Example 1 can be used as an excellent calcineurin activity inhibitor.

Example 6

In the present Example, before preparation of a plant extract, American angelica was subjected to preliminary washing with aqueous ethanol solutions of different concentrations. Firstly, American angelica was washed once with 10 to 60 vol. % ethanol, and then a plant extract was prepared (samples 1 to 6), More specifically, 8 g (total amount) of 5 mm×5 mm cut pieces of Angelica root were immersed in 160 mL each of 10 to 60 vol. % ethanol for one day with stirring, and then the extract (wash liquid) was removed. Subsequently, the thus-washed pieces were extracted with 80 mL of anhydrous ethanol for three days, to thereby yield an extract (see Table 2 below).

TABLE 2

| Sample | Preliminary washing liquid |
|---|---|
| Sample 1 | 10% ethanol |
| Sample 2 | 20% ethanol |
| Sample 3 | 30% ethanol |
| Sample 4 | 40% ethanol |
| Sample 5 | 50% ethanol |
| Sample 6 | 60% ethanol |

In the next case, American angelica was washed once or a plurality times with 30 vol. % ethanol, and then a plant extract was prepared (samples 7 to 17). More specifically, 8 g (total amount) of 5 mm×5 mm cut pieces of Angelica root were immersed in 80 mL, 160 mL, or 320 mL of 30 vol. % ethanol for one day with stirring, then the extract (wash liquid) was removed. This procedure was 1 to 9 times. Subsequently, the thus-washed pieces were extracted with 80 mL of anhydrous ethanol for three days, to thereby yield an extract (see Table 3 below).

TABLE 3

| Sample | Amount of preliminary washing liquid (mL) | No. of washing times (times) |
|---|---|---|
| Sample 7 | 80 | 1 |
| Sample 8 | 80 | 3 |
| Sample 9 | 80 | 5 |
| Sample 10 | 80 | 7 |
| Sample 11 | 80 | 9 |
| Sample 12 | 160 | 3 |
| Sample 13 | 160 | 5 |
| Sample 14 | 160 | 7 |
| Sample 15 | 320 | 1 |
| Sample 16 | 320 | 3 |
| Sample 17 | 320 | 5 |

In the second case, a plant extract was prepared without performing the preliminary washing, for comparison (sample 18). More specifically, 8 g (total amount) of 5 mm×mm cut pieces of Angelica root were extracted with 80 mL of anhydrous ethanol for three days, to thereby yield an extract (sample 18).

In a manner similar to that employed in Example 2, NFAT signaling inhibitory activity of each of the thus-prepared samples 1 to 18 was determined. Also, photosensitizing substance (5-MOP or 8-MOP) content of each of the samples 1 to 18 was determined through HPLC as follows. Firstly, a predetermined amount of 5-MOP or 8-MOP was dissolved in methanol, to thereby prepare 1, 5, 10, 100, 1000 ppm solution of 5-MOP or 8-MOP. 5 μL of each solution was analyzed through HPLC, and a calibration curves were drawn from UV absorption peak area data. Under the same conditions, 5 μL each of the samples 1 to 18 was analyzed through high performance liquid chromatography (HPLC), and the concentration was determined from the UV absorption peak area with the corresponding calibration curve. For each sample, measurement was performed three times, and the three values were averaged. HPLC analysis was performed by means of Agilent 1100 Series under the following conditions: C18 reverse phase column (Inertsil ODS-3:4 μM ϕ: 2.1×150 mm); flow rate 0.2 mL/min; eluent (acetonitrile/0.1% formic acid=0/100 (0 min)→100/0 (30 min)→100/0 (40 min)); temperature 40° C.; and detection at UV 254 nm. The retention times of 5-MOP and 8-MOP were 14.7 min and 13.6 min, respectively.

Table 4 shows the NFAT signal inhibitory activity, 5-MOP concentrations, and 8-MOP concentrations of samples 1 to 18.

TABLE 4

| Sample | Washing soln. | Solvent (mL) | Washing times | Vaporization residue (w/v %) | NFAT transcription inhibition activity (%) | 8-MOP concn. (ppm) | 5-MOP concn. (ppm) |
|---|---|---|---|---|---|---|---|
| Sample 1 | 10 ET | 160 | 1 | 0.7 | 60.36 | 3.1 | 18 |
| Sample 2 | 20 ET | 160 | 1 | 0.67 | 59.43 | 3 | 19.7 |
| Sample 3 | 30 ET | 160 | 1 | 0.56 | 59.89 | 1.7 | 4.5 |
| Sample 4 | 40 ET | 160 | 1 | 0.44 | 33.75 | 1.3 | 6.3 |
| Sample 5 | 50 ET | 160 | 1 | 0.35 | 3.64 | — | 1.1 |
| Sample 6 | 60 ET | 160 | 1 | 0.31 | 13.11 | — | 3.8 |
| Sample 7 | 30 ET | 80 | 1 | 0.83 | 67.65 | 4.5 | 18.3 |
| Sample 8 | 30 ET | 80 | 3 | 0.29 | 55.44 | — | 1.5 |
| Sample 9 | 30 ET | 80 | 5 | 0.15 | 50.96 | — | 1.3 |
| Sample 10 | 30 ET | 80 | 7 | 0.15 | 28.38 | — | — |
| Sample 11 | 30 ET | 80 | 9 | 0.15 | 38.93 | — | — |
| Sample 12 | 30 ET | 160 | 3 | 0.22 | 49.1 | — | 2 |
| Sample 13 | 30 ET | 160 | 5 | 0.19 | 44.97 | — | — |
| Sample 14 | 30 ET | 160 | 7 | 0.18 | 37.97 | — | — |
| Sample 15 | 30 ET | 320 | 1 | 0.52 | 56.51 | 1.8 | 2.8 |
| Sample 16 | 30 ET | 320 | 3 | 0.2 | 26.13 | — | — |
| Sample 17 | 30 ET | 320 | 5 | 0.19 | 22.9 | — | — |
| Sample 18 | — | — | 0 | 0.5 | 67.0 | 2.1 | 23.1 |
| 50 nM CsA | | | | | 99.9 | | |

As is clear from Table 4, the photosensitizing substance level was found to be reduced through preliminary washing plant Angelica with aqueous ethanol. In particular, when preliminary washing was performed with 30 to 40 vol. % ethanol, the 8-MOP level and 5-MOP level (photosensitizing substance level index) were found to be considerably reduced, while NFAT signaling inhibitory activity was maintained. As is also clear from Table 4, when 30 to 40 vol. % ethanol was used, the photosensitizing substance level was found to be reduced to a detection limit or lower through performance of preliminary washing a plurality of times. Thus, the experiments of the Examples have revealed that performance of preliminary washing with 25 to 45 vol. % aqueous ethanol can provide a plant extract substantially containing no photosensitizing substance and maintaining high NFAT signal inhibitory activity.

What is claimed is:

1. A method of treating psoriasis or atopic dermatitis in a human in need thereof consisting essentially of administering a therapeutically effective amount of an aqueous ethanol or anhydrous ethanol extract of American angelica root to said human to treat the psoriasis or atopic dermatitis in said human.

* * * * *

```
SEQUENCE LISTING

<160> NUMBER OF SEQ ID NOS: 2

<210> SEQ ID NO 1
<211> LENGTH: 30
<212> TYPE: DNA
<213> ORGANISM: Artificial
<220> FEATURE:
<223> OTHER INFORMATION: synthesized

<400> SEQUENCE: 1
ggaggaaaaa ctgtttcata cagaaggcgt                                     30

<210> SEQ ID NO 2
<211> LENGTH: 18
<212> TYPE: PRT
<213> ORGANISM: Artificial
<220> FEATURE:
<223> OTHER INFORMATION: synthesized
<220> FEATURE:
<221> NAME/KEY: MOD_RES
<222> LOCATION: (14)..(14)
<223> OTHER INFORMATION: PHOSPHORYLATION

<400> SEQUENCE: 2

Asp Leu Asp Val Pro Ile Pro Gly Arg Phe Asp Arg Val Ser Val Ala
1               5                   10                  15

Ala Glu
```